United States Patent [19]

Wulf

[11] Patent Number: 5,066,124
[45] Date of Patent: Nov. 19, 1991

[54] ATOMIC ABSORPTION SPECTROPHOTOMETER FOR SIMULTANEOUS MULTI-ELEMENT ANALYSIS

[75] Inventor: Jurgen Wulf, Uberlingen, Fed. Rep. of Germany

[73] Assignee: Bodenseewerk Perkin Elmer GmbH, Uberlingen, Fed. Rep. of Germany

[21] Appl. No.: 513,395

[22] Filed: Apr. 23, 1990

[30] Foreign Application Priority Data

Jul. 21, 1989 [DE] Fed. Rep. of Germany ....... 3924060

[51] Int. Cl.$^5$ ............... G01N 21/71; G01N 21/74; G01J 3/36
[52] U.S. Cl. ................................... 356/312; 356/326
[58] Field of Search .............. 356/312, 326, 328, 320

[56] References Cited

U.S. PATENT DOCUMENTS

| 4,257,707 | 3/1981 | Liertz et al. | 356/73.1 |
| 4,575,241 | 3/1986 | Demers et al. | 356/316 |
| 4,750,800 | 6/1988 | Fournier et al. | 350/96.11 |

FOREIGN PATENT DOCUMENTS

52-6586 1/1977 Japan ................................... 356/328

Primary Examiner—Vincent P. McGraw
Attorney, Agent, or Firm—Thomas P. Murphy; Edwin T. Grimes

[57] ABSTRACT

In an atomic absorption spectrophotometer for multielement analysis, the light from a plurality of light sources each of which emits the resonance lines of one associated looked-for element is superimposed into a single light beam by means of interconnected light guides. The light is directed onto a polychromator 64 via an optical coupler.

4 Claims, 2 Drawing Sheets

ATOMIC ABSORPTION SPECTROPHOTOMETER FOR SIMULTANEOUS MULTI-ELEMENT ANALYSIS

TECHNICAL FIELD

The invention relates to an atomic absorption spectrophotometer for simultaneous measurement of atomic absorption with a plurality of elements, comprising:

a plurality of line-emitting light sources, each of which emits the resonant lines of one or several looked-for elements;

means for superimposing the radiation originating from the line-emitting light sources to one light beam;

an atomizing device for atomizing an examined sample and for generating an atomic vapor in which the looked-for elements from the sample are present in their atomic state;

optical means for passing the measuring light beam through the atomic vapor; and detector means for a separate detection of the absorptions to which the resonant lines of the different looked-for elements in the sample are subjected.

BACKGROUND ART

In atomic absorption spectroscopy a sample is atomized by a flame or by an electrically heated furnace, so that the elements contained in the sample are present in their atomic state. A measuring light beam from a light source which emits characteristic resonant lines of a looked-for element is passed through the atomic vapor generated in this way. Each of the atoms absorbs only radiation with the resonant lines being characteristic of one element. Light having other wavelengths is not absorbed by the atoms of the atomic vapor. Thereby, the measuring light beam is subjected to an absorption which is a measure of the number of the atoms of the looked-for element in the atomic vapor.

The light source is usually a hollow cathode lamp in which a gas discharge with the atoms of the looked-for element takes place. These hollow cathode lamps emit the spectrum of the looked-for element. From this spectrum, a certain resonant line is chosen by a monochromator. The measuring light beam with this resonant line is passed through the atomized sample and impinges onto a photoelectric detector, usually a photomultiplier. With such an arrangement only one single element, at a time, can be measured.

Atomic absorption spectrometers are known in which several different hollow cathode lamps are arranged on a rotatable carrier. One of these hollow cathode lamps, at a time, is moved into an operative position in which it generates the measuring light beam. Thereby, different elements can be measured consecutively. In analyses with electrothermal atomization of the sample in an electrically heated furnace, a separate sample has to be introduced into the furnace for each determination.

DISCLOSURE OF THE INVENTION

It is the object of the invention to design an atomic absorption spectrophotometer of the type mentioned above, for the simultaneous measurement of the atomic absorption with a plurality of elements, so that, without unallowably high light losses, the measuring light beams can be superimposed from a larger number of line-emitting sources.

According to the invention this object is achieved in that;

light from each light source is guide in an associated light guide which does not absorb light in the used spectral range;

the means for superimposing the radiation are formed by optical coupler means by which the light guides associated with the different light sources are coupled to a common exit light guide; and the exit light guide extends to the atomizing device.

The superimposing of the measuring light beams according to the invention is not made by mirrors. On the contrary, each measuring light beam is guided in a light guide, a light guiding fiber, for example. These light guides communicate by optical coupler means with the exit light guide. The exit light guide extends to the atomizing device. Thereby, no multiplicating light losses occur as it is the case when light beams are superimposed by means of semi-transparent mirrors.

The optical coupler means can comprise an integrated optical system in which entrance-side light guides are joined two by two in Y-shape and form an exit-side light guide. The entrance-side light guides communicate with the light guiding fibers each of which extends to a light source, these light guiding fibers representing said associated light guides. The exit light guide extending to the atomizing device is connected to an exit-side light guide of the integrated optical system. In this way, the light flow in the different light guiding fibers can be superimposed with smaller losses. The integrated optical system may comprise several stages of light guides joined in Y-shape, each of the exit-side light guides of the entrance-side stage forming an entrance-side light guide of the next exit-side stage.

The detector means may be formed by a polychromator.

An embodiment of the invention will now be described in further detail with reference to the accompanying drawings.

PREFERRED EMBODIMENT OF THE INVENTION

Figure 1:
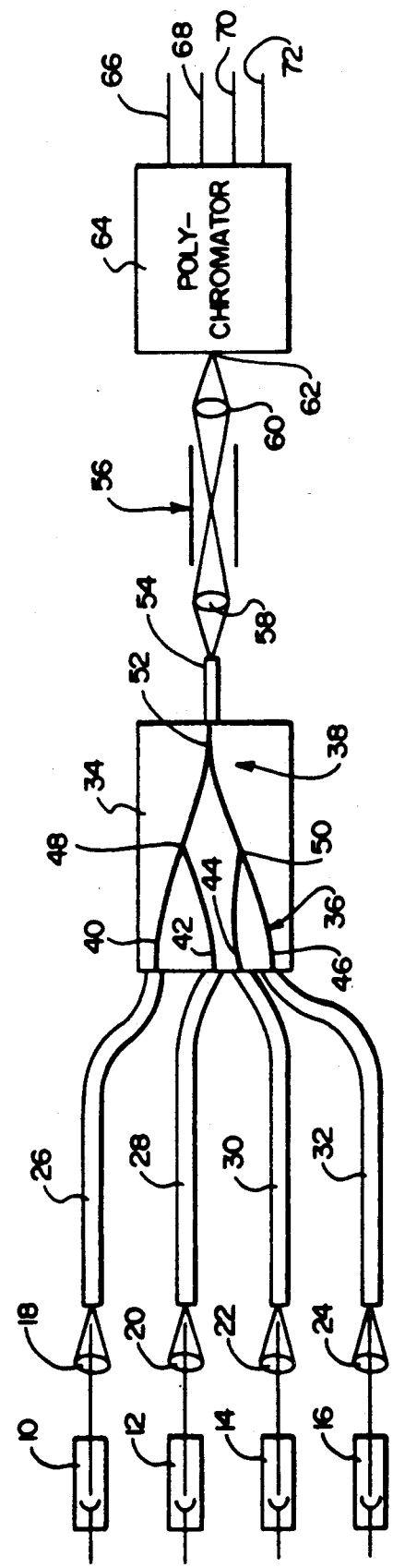
FIG. 1 is a schematic illustration of an atomic absorption spectrophotometer for simultaneous measurement of the absorption of a plurality of elements.

In FIG. 1, there are shown four line emitting light sources 10, 12, 14 and 16 in the form of hollow cathode lamps. Each of the light sources 10, 12, 14 and 16 emits a light spectrum which is characteristic of a certain looked-for element and are therefore, associated with different elements. The light originating from the light sources 10, 12, 14 and 16 is focused by focussing lenses 18, 20, 22 and 24, respectively, on the end face of an associated light guide 26, 28, 30 and 32, respectively.

Numeral 34 designates coupler means which is here designed as an integrate optical system. The integrated optical system of the coupler means comprises two stages 36 and 38 of light guides which are joined in Y-shape. In the first stage 36, four entrance-side light guides 40, 42, 44 and 46 are joined two by two in a Y-shape. These form two exit-side light guides 48 and 50. The exit-side light guides 48 and 58 of the first stage 36 form the entrance-side light guides of the next exit-side stage 38. The light guides 48 and 50 are joined in Y-shape and form an exit-side light guide 52.

Each of the entrance-side light guides 40, 42, 44 and 46 communicates with one of the light guiding fibers 26, 28, 30 and 32, respectively, each of which extends to one of the light sources 10, 12 14 and 16 and represents an associated light guide. The exit-side light guide 52 of the integrated optical system 34 communicates with an exit light guide 54 which extends to the atomizing device 56.

The atomizing device 56 is a conventional graphite tube for the electro-thermal atomization of the sample. By a lens 58, the light beam originating from the exit light guide 54 is focussed in the center of the graphite tube A lens 60 on the exit side of the graphite tube focusses the light beam onto the entrance slit 62 of a polychromator 64. The polychromator 64, in a well-known way, generates a spectrum which comprises the line spectra of the four light sources 10, 12, 14 and 16. At the location of characteristic resonant lines of the looked-for elements, detectors are provided which provide signals at the outputs 66, 68, 70 and 72.

Figure 2:
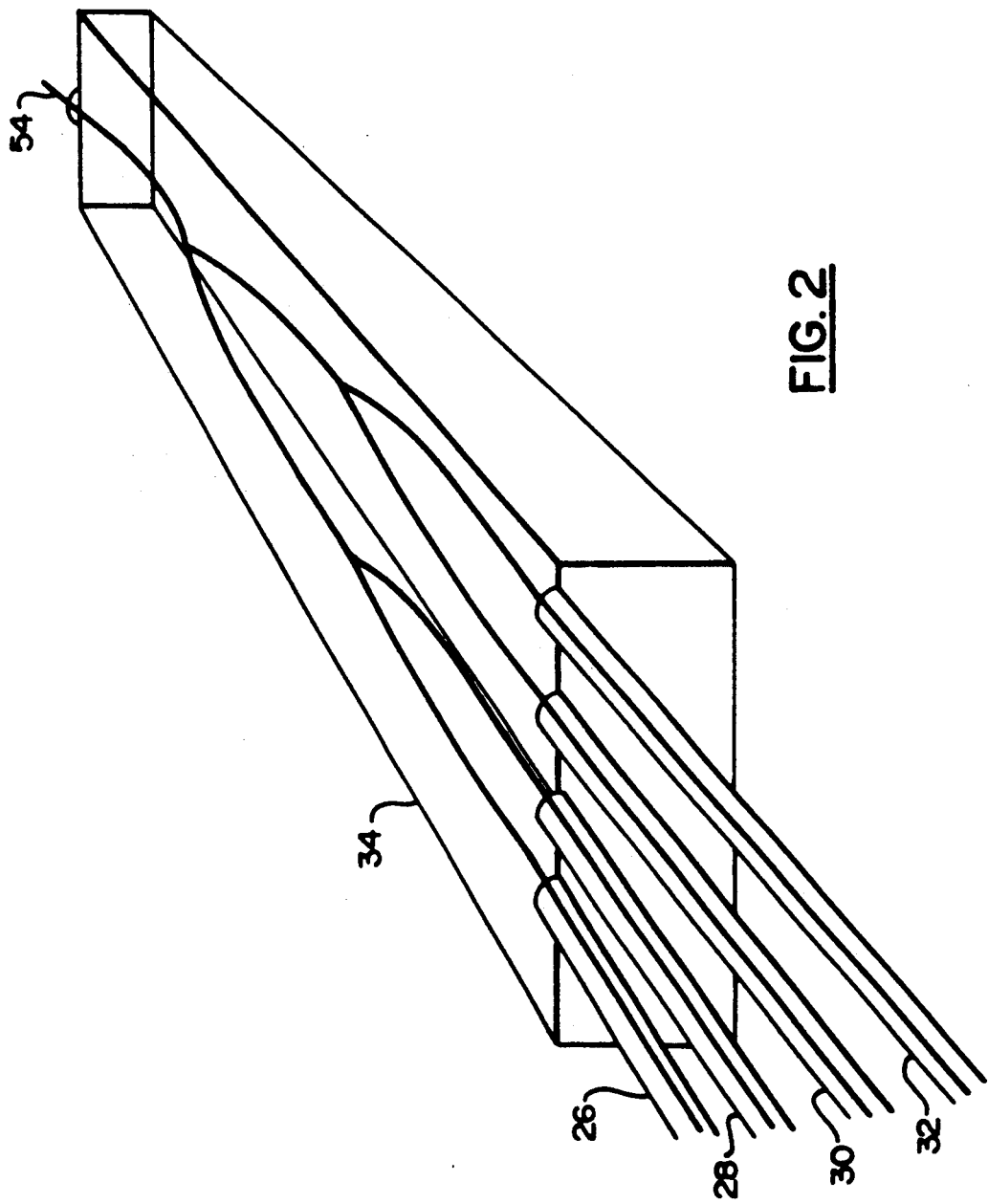
FIG. 2 is a perspective illustration and shows the integrated optical system serving as coupler means with the light guides associated with the light sources and the exit light guide extending to the atomizing device.

FIG. 2 is a perspective illustration of the integrate optical system serving as coupler means 34 and the light guiding fibers 26, 28, 30, 32 and 54, respectively, connected thereto.

Any number of elements may be identified and measured by increasing the number of light sources and associated light guide means.

What is claimed is:

1. Atomic absorption spectrophotometer for simultaneous measurement of atomic absorption of a plurality of elements, comprising:
    a plurality of line-emitting light sources for simultaneously emitting resonant lines of respective ones of a plurality of looked-for elements;
    optical coupler means for superimposing upon each other the resonant lines simultaneously originating from said plurality of line-emitting light sources in order to form a single light beam containing the superimposed resonant lines from the plurality of line-emitting light sources;
    an atomizing device for atomizing a sample under investigation and for generating an atomic vapor in which the looked-for elements of the sample are present in their atomic state;
    optical means for passing the single light beam through the atomic vapor;
    detector means for receiving said single light beam after passage through said atomic vapor, for separately detecting the absorptions to which the resonant lines of the different looked-for elements in the sample are subjected;
    light guide means which only insignificantly absorb light in the spectral range of the resonant lines emitted by the plurality of line-emitting light sources;
    said light guide means being disposed intermediate said plurality of line-emitting light sources and said optical coupler means, for guiding the emitted resonant lines from the line-emitting light sources to said optical coupler means;
    said optical coupler means constituting an integrated optical system containing a plurality of entrance-side light guides for receiving the emitted resonant lines from said light guide means, and a common exit-side light guide which is coupled to said entrance-side light guides; and
    an exit light guide coupled to said common exit-side light guide of said optical coupler means for directing said single light beam from said optical coupler means to said atomizing device.

2. Atomic absorption spectrophotometer as set forth in claim 1, wherein:
    said plurality of entrance-side light guides in said optical coupler means are joined two by two in Y-shapes defining respective exit-side light guides;
    said light guide means constituting optical fibers for coupling said line-emitting light sources to respective ones of said entrance-side light guides in said optical coupler means; and
    said exit-side light guides are connected to said common exit-side light guides.

3. Atomic absorption spectrophotometer as set forth in claim 2, wherein said integrated optical system of said optical coupler means comprises a series of Y-shaped stages, each exit-side light guide of one of said Y-shaped stages forming one of the entrance-side light guides of the Y-shaped stage which is the next in the series.

4. Atomic absorption spectrophotometer as set forth in one of claim 3 wherein said detector is a polychromator.

* * * * *

UNITED STATES PATENT AND TRADEMARK OFFICE
CERTIFICATE OF CORRECTION

PATENT NO. : 5,066,124
DATED : Nov. 19, 1991
INVENTOR(S) : Jurgen Wulf

It is certified that error appears in the above-identified patent and that said Letters Patent is hereby corrected as shown below:

Column 4, line 47, insert --means-- after "detector".

Signed and Sealed this

Eighteenth Day of May, 1993

Attest:

MICHAEL K. KIRK

Attesting Officer

Acting Commissioner of Patents and Trademarks